United States Patent
Lucchini et al.

(10) Patent No.: US 12,016,735 B2
(45) Date of Patent: Jun. 25, 2024

(54) TEMPLATE AND METHOD FOR MEASURING THE CROSS SECTION OF A GRAFT

(71) Applicant: MEDACTA INTERNATIONAL SA, Castel San Pietro (CH)

(72) Inventors: Riccardo Lucchini, Castel San Pietro (CH); Sascha Berberich, Castel San Pietro (CH); Francesco Siccardi, Castel San Pietro (CH); Gianluca Parisi, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 452 days.

(21) Appl. No.: 17/598,090

(22) PCT Filed: Mar. 24, 2020

(86) PCT No.: PCT/IB2020/052735
§ 371 (c)(1),
(2) Date: Sep. 24, 2021

(87) PCT Pub. No.: WO2020/194178
PCT Pub. Date: Oct. 1, 2020

(65) Prior Publication Data
US 2022/0168062 A1 Jun. 2, 2022

(30) Foreign Application Priority Data
Mar. 26, 2019 (IT) .................. 102019000004331

(51) Int. Cl.
*A61B 5/107* (2006.01)
*A61B 90/00* (2016.01)
*A61F 2/08* (2006.01)

(52) U.S. Cl.
CPC ............... *A61B 90/06* (2016.02); *A61F 2/08* (2013.01); *A61B 2090/061* (2016.02)

(58) Field of Classification Search
CPC ....... A61B 90/06; A61B 90/061; A61B 5/107; A61B 5/1072; G01B 3/34
(Continued)

(56) References Cited

U.S. PATENT DOCUMENTS 3,548,506 A * 12/1970 Harrington ............... G01B 3/34
D10/64
5,251,642 A 10/1993 Handlos
(Continued)

FOREIGN PATENT DOCUMENTS

ES 2359835 T3 5/2011

OTHER PUBLICATIONS

International Search Report and Written Opinion issued in PCT/IB2020/052735, dated Aug. 21, 2020, 10 pages.

*Primary Examiner* — George B Bennett
(74) *Attorney, Agent, or Firm* — Meunier Carlin & Curfman LLC

(57) ABSTRACT

A template for measuring the cross section of a graft comprises a first half-body and a second half-body. The two half-bodies are mutually secured such that they can rotate the one with respect to the other around an axis, each one of the two half-bodies comprises a plurality of openings having known and different sizes, each one of the openings of the two half-bodies is open toward the outside through an at least partially radial slot. The two half-bodies can rotate the one with respect to the other around the axis between an open position and a closed position and vice versa. In the open position the slots of the first half-body axially coincide with the slots of the second half-body, and in the closed
(Continued)

position the openings of the first half-body axially coincide with the openings of the second half-body.

13 Claims, 11 Drawing Sheets

(58) Field of Classification Search
USPC ......... 33/511, 512, 555.1, 555.2, 514.1, 562, 33/563
See application file for complete search history.

(56) References Cited

U.S. PATENT DOCUMENTS

| | | | |
|---|---|---|---|
| 5,397,357 A | 3/1995 | Morgan et al. | |
| 5,814,098 A * | 9/1998 | Hinnenkamp | A61F 2/2496 600/587 |
| 6,892,466 B2 * | 5/2005 | Kurz | A61F 2/18 600/587 |
| 7,225,554 B2 * | 6/2007 | Madsen | A61B 5/107 600/587 |
| 7,603,788 B2 * | 10/2009 | Kurz | A61F 2/18 600/587 |
| 8,728,012 B2 * | 5/2014 | Braido | A61B 5/6876 33/759 |
| 10,426,460 B2 * | 10/2019 | Taber | A61B 17/0401 |
| 10,874,527 B2 * | 12/2020 | Fulton | A61B 17/1764 |
| 11,033,281 B2 * | 6/2021 | Erickson | A61B 17/157 |
| 11,241,293 B2 * | 2/2022 | Hodorek | A61B 17/1686 |
| 11,274,911 B1 * | 3/2022 | Chang | G01B 5/213 |
| 11,337,830 B2 * | 5/2022 | Rodriguez | G01B 3/56 |
| 11,389,366 B2 * | 7/2022 | Peyrl | A61B 5/1121 |
| 11,419,595 B2 * | 8/2022 | Salvermoser | A61B 17/025 |
| 2004/0107592 A1 * | 6/2004 | Matlis | A61B 5/225 33/512 |
| 2005/0235505 A1 * | 10/2005 | Joseph | G01B 3/34 33/501.45 |
| 2006/0090362 A1 * | 5/2006 | Wood | A61B 5/107 33/512 |
| 2007/0150057 A1 | 6/2007 | Kurz et al. | |
| 2016/0143695 A1 | 5/2016 | Reinke | |

* cited by examiner

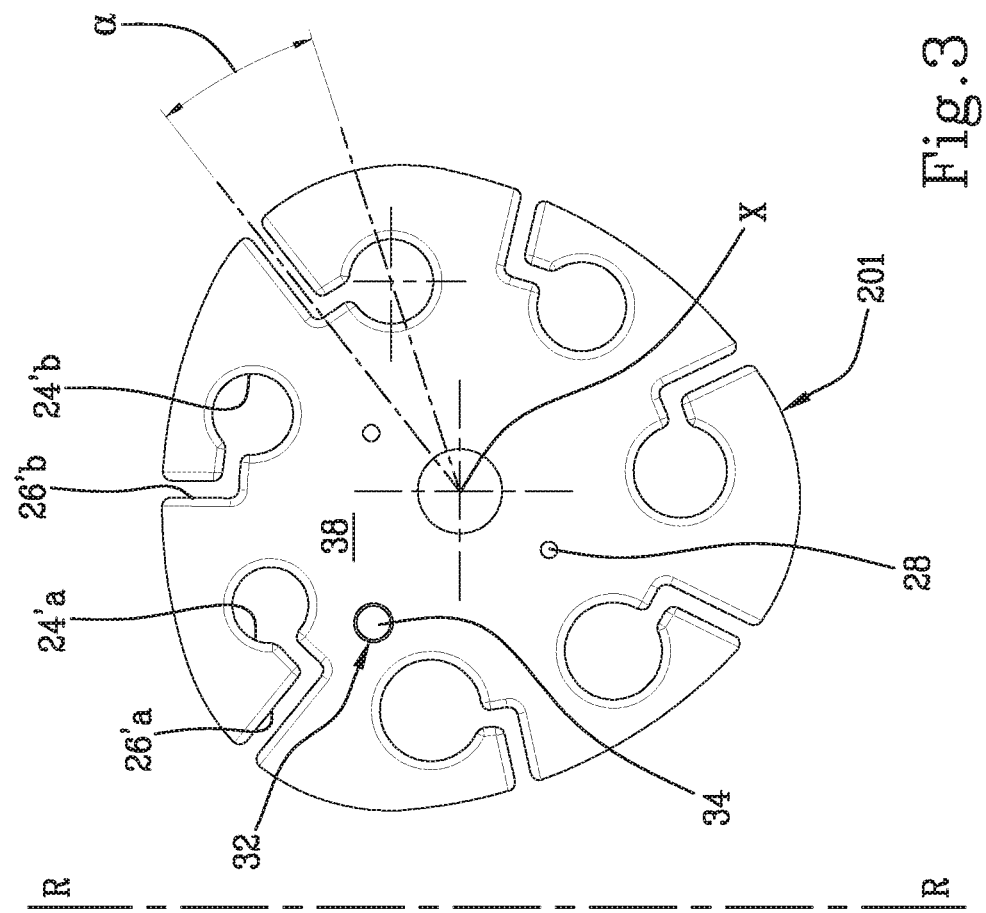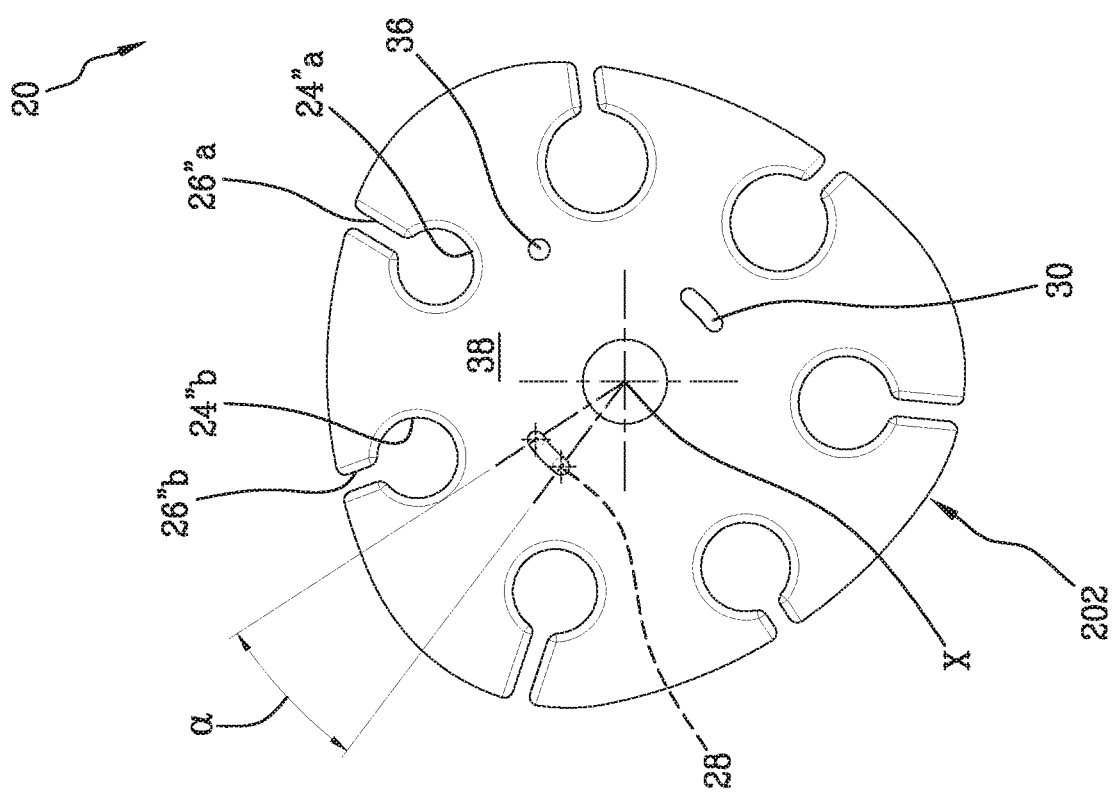
Fig.3

TEMPLATE AND METHOD FOR MEASURING THE CROSS SECTION OF A GRAFT

The present invention relates to a template for measuring tendon grafts, in particular a template for measuring the cross section of a graft. The present invention also relates to a method for measuring the cross section of a graft.

In the field of surgical procedures for the reconstruction of ligaments and tendons, it is known to insert a portion of tendon, commonly referred to as a graft, intended for replacing the consumed segment of the original tendon. The graft can have different origins: it can be obtained from the patient himself, and is therefore referred to as an autograft; or it can be obtained from a donor, and in this case, it is referred to as an allograft; finally, it can be formed artificially.

In order to restore full functionality of the joint, the graft should be solidly and reliably connected to the patient's bone. To this end, an ad hoc tunnel is made in the bone, and the graft is introduced into the tunnel and held in place until the osseointegration is achieved establishing the definitive merging of the graft to the bone. Suture threads are usually applied to the two ends of the graft to reinforce the graft and achieve the temporary mechanical connection. The suture threads connect the graft to the fixation implant and—through the so-called reinforcement step—make the graft stiffer at its ends. In addition, the suture threads are also easier to insert into the bone tunnel than the graft and, once inserted, allow the desired graft segment to be pulled into the tunnel. The optimal outcome of the intervention is achieved when the inner diameter of the bone tunnel is substantially equal to the outer diameter of the graft. This way, the two surfaces are in contact without interference, thereby facilitating the osseointegration.

During the operation, it is therefore necessary for the surgeon to measure the cross section of the graft in the segment to be introduced into the tunnel. Such measurement is not easy, since the graft is an elongated structure consisting of a tissue which is rather yielding, especially in the transverse direction. That is, whether natural or artificial, the tissue of the graft tends to deform when contacted by a measurement matching part. To date, a static measuring template of the type shown schematically in FIG. 1 is used to make such measurement. The measuring template of the known type comprises a body, e.g. disc-shaped, comprising a series of calibrated openings of different and known sizes. Each opening is placed in communication with the outside through a slot. The use of the known measuring template is as follows. The surgeon estimates a plausible size of the graft and identifies in the measuring template the first-attempt opening corresponding to such size. The suture threads connected to the graft are introduced, through the slot thereof, into the first-attempt opening. Then the template is slid along the suture threads until it approximates the first-attempt opening to the end of the graft. If the graft enters the opening easily and without clearance, the latter defines the correct size of the graft, and the bone tunnel is made based on such size. Alternatively, it is possible to proceed with a second attempt, trying another larger or smaller opening, depending on the result of the first attempt. This way, by subsequent attempts, it is possible to identify the opening where the graft enters without clearance and without interference.

Such procedure, although widely used, is not free from shortcomings. In fact, due to the characteristics of transverse yieldability of the tissue forming the graft, it is possible that the latter partially expands beyond the calibrated opening to partially occupy the relative access slot. This way, since the calibrated opening accommodates only a part of the cross section of the graft, the size that is being derived therefrom will be underestimated, and the bone tunnel that will be made will be slightly too small compared to the real needs.

Accordingly, the procedure may result in a graft being forced into a too small tunnel, thereby not achieving an optimal osseointegration. Alternatively, if the surgeon immediately notices the error, the tunnel may be enlarged by reaming, however increasing the risks and timing of the operation.

Therefore, the object of the present invention is to overcome the drawbacks underlined before with respect to the prior art.

In particular, it is a task of the present invention to provide a measuring template and method respectively allowing the cross section of a graft to be determined without any risk of error.

Furthermore, it is a task of the present invention to provide a measuring template and method that can continue to provide the advantages of solutions of known type, in addition to the advantages introduced.

This object and these tasks are achieved by a measuring template according to claim 1 and by a measuring method according to claim 9.

To better understand the invention and appreciate its advantages, some of its exemplifying and non-limiting embodiments are described below with reference to the accompanying drawings, wherein:

FIG. 3 shows an axial view of the graft measuring template in FIG. 2, in a disassembled configuration;

In the context of the present discussion, some terminological conventions have been adopted in order to make reading easier and smoother. These terminological conventions are clarified below with reference to the accompanying figures.

The template according to the invention uniquely defines a rotation axis X. Axial direction thus means the direction of any line parallel to the axis X. Radial direction means the direction of any half-line having its origin on the axis X and perpendicular thereto. Circumferential (or, respectively, tangential) direction means the direction of any circumference (or, respectively, of a tangent thereof) being centred on the axis X and lying on a plane perpendicular thereto.

Figure 1:
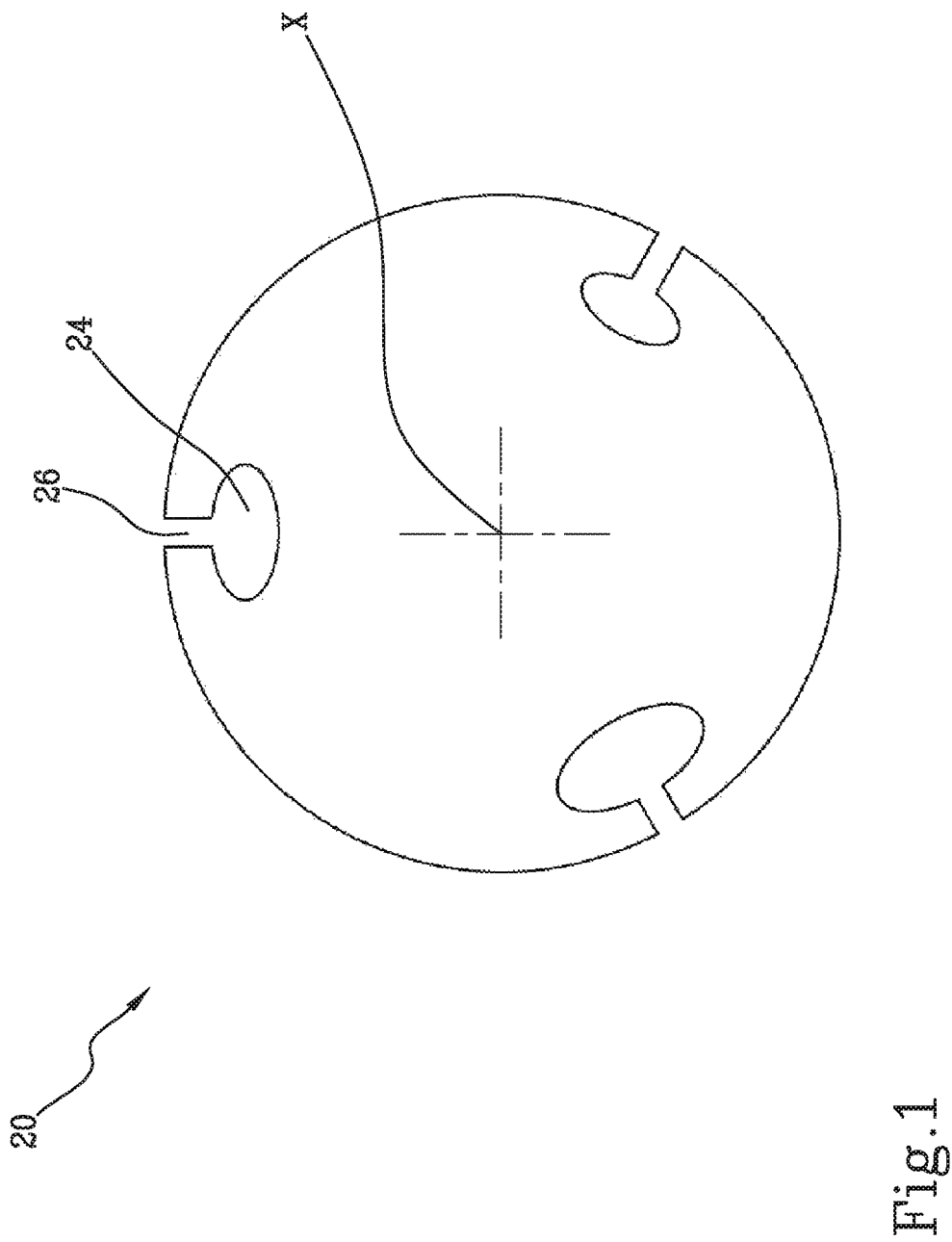
FIG. 1 shows an axial schematic view of a graft measuring template according to the prior art.

The same convention is also employed to describe the prior art solution, shown in FIG. 1. Although there are no moving parts in this solution, and there is therefore no axis of rotation, however, the discoidal shape of the template and the manifest geometric analogy with the solution of the invention suggest a unique, yet intuitive, application of the terms axial, radial, circumferential and tangential.

According to a first aspect thereof, the invention relates to a template 20 for measuring the cross section of a graft 22. The template 20 according to the invention comprises a first half-body 201 and a second half-body 202, wherein:

the two half-bodies 201, 202 are mutually secured such that they can rotate the one with respect to the other around an axis X;

each one of the two half-bodies 201, 202 comprises a plurality of openings 24 having known and different sizes;

each one of the openings 24 of the two half-bodies 201, 202 is open toward the outside through an at least partially radial slot 26.

Furthermore, in the template 20 according to the invention, the two half-bodies 201, 202 can rotate the one with respect to the other around axis X between an open position A and a closed position C and vice versa, wherein in the open position A the slots 26 of the first half-body 201 axially coincide with the slots 26 of the second half-body 202; and in the closed position C the openings 24 of the first half-body 201 axially coincide with the openings 24 of the second half-body 202.

The openings 24 are preferably arranged in proximity of the radial periphery of the two half-bodies 201, 202. This way, it is possible to limit the length of the slots 26 through which the openings 24 open toward the outside.

Preferably, the mutual rotation of the two half-bodies 201, 202 is limited within a predefined angle $\alpha$, at the ends of which there are the open position A and the closed position C. The mutual rotation can be limited, for example, by limit switches defining a support in the circumferential direction. In FIG. 3, for example, the pins 28 extending in an axial direction from the first half-body 201 and designed to be accommodated within the arched eyelets 30 formed in the second half-body 202 are visible. The arched eyelets 30 define the two circumferential limit switches for the pins 28.

Preferably, the template 20 comprises a stop 32 of the spring-loaded ball type, well known per se, suitable for marking the reaching of the closed position C. In such a type of stop, a ball 34 pushed in the axial direction by a spring is arranged on the inner surface 38 of a half-body (e.g. the first half-body 201 in FIG. 3) and a seat 36 suitable for accommodating the ball 34 is arranged on the inner surface 38 of the other half-body (e.g. the second half-body 202 in FIG. 3). During the relative rotation between the two half-bodies 201, 202, the ball 34 rolls on the inner surface 38 of the second half-body 202, when the template 20 reaches the closed position C, the ball 34 snaps into the seat 36. This way, the ball stop 32 transmits to the user a distinct sensation when the relative rotation of the two half-bodies 201, 202 leads the template 20 to the closed position C. This feature is particularly advantageous since the evaluation of the size of the graft 22 must be carried out with the template 20 in the closed position C. An evaluation performed with the template 20 in an intermediate position between the open position A and the closed position C would return an incorrect size for the graft 22, typically returning a size of the graft 22 greater than the actual one.

As can be seen in the accompanying figures, each of the two half-bodies 201, 202 comprises a series of openings $24_a$, $24_b$, $24_c$ . . . . Here and below, indexes are introduced that allow, when needed for the sake of more clarity, a distinction between the various openings 24 and the respective slots 26. The subscripted alphabetical indexes a, b, c . . . indicate the different size of each of the openings 24 and, therefore, the slot 26 corresponding thereto. Conversely, the single ' and double '' inverted commas indicate that an opening 24 or a slot 26 belongs to the first half-body 201 or to the second half-body 202, respectively.

Figure 2:
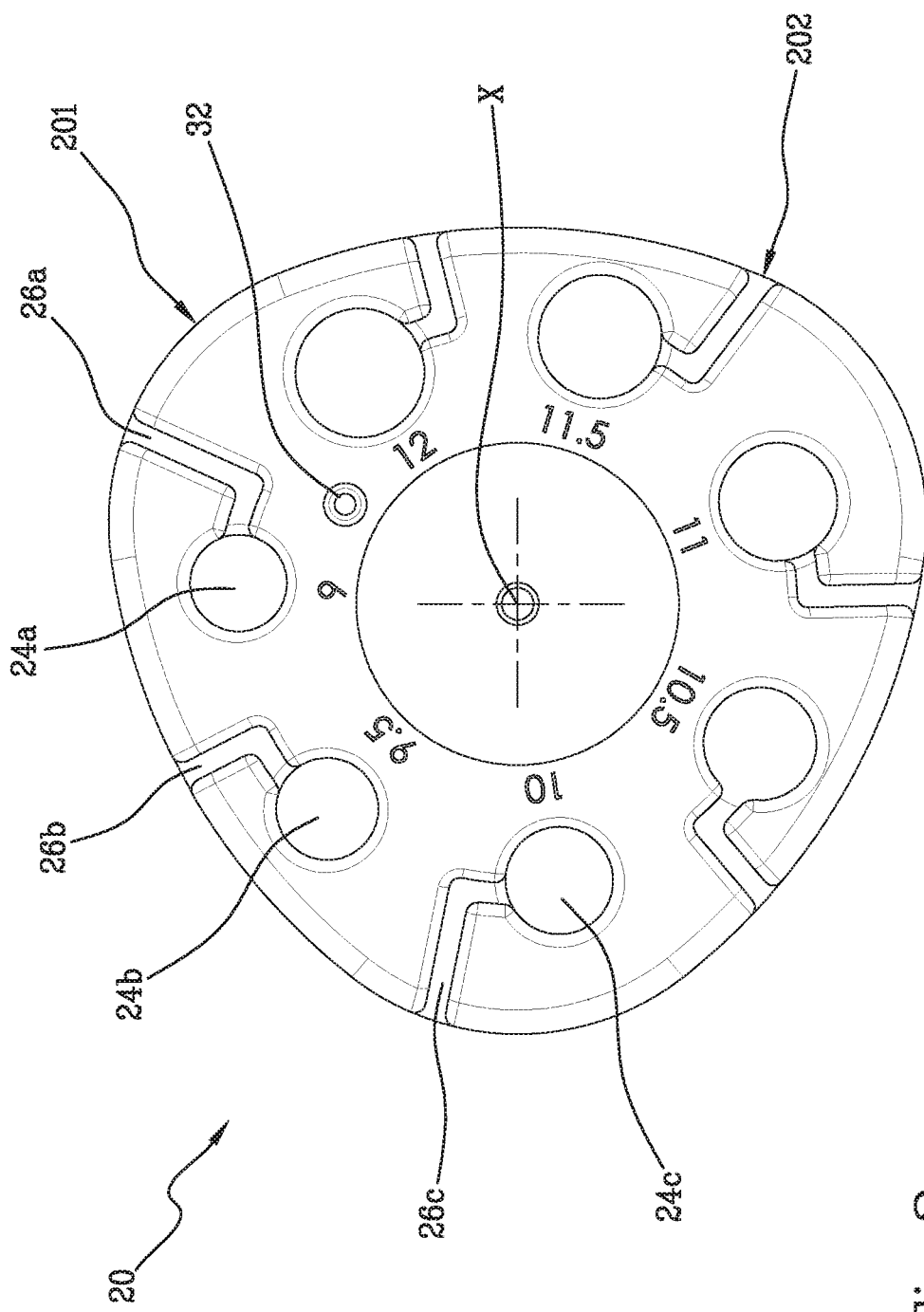
FIG. 2 shows an axial view of a graft measuring template according to the invention.
Figure 4:
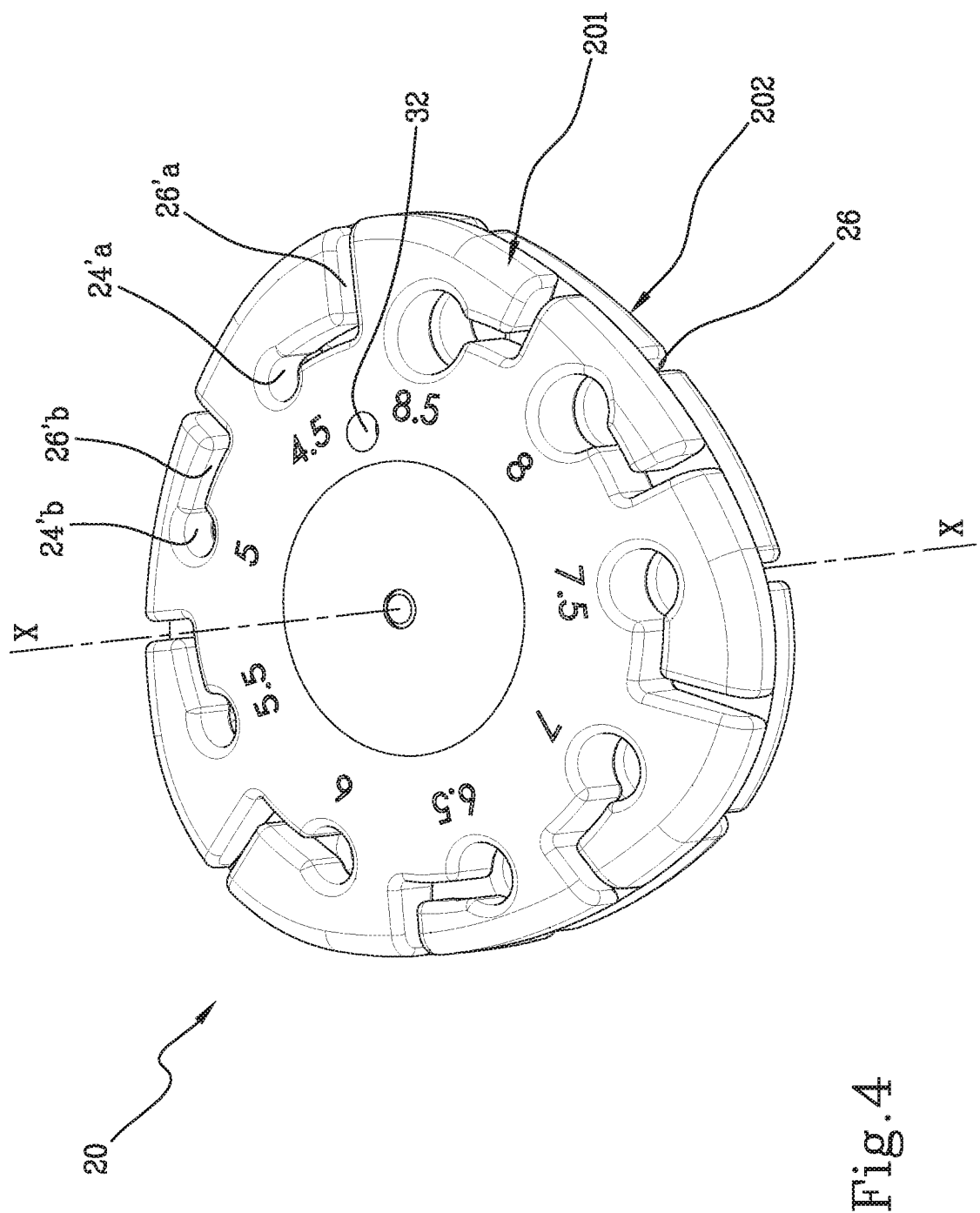
FIG. 4 shows a perspective view of a graft measuring template according to the invention.
Figure 5:
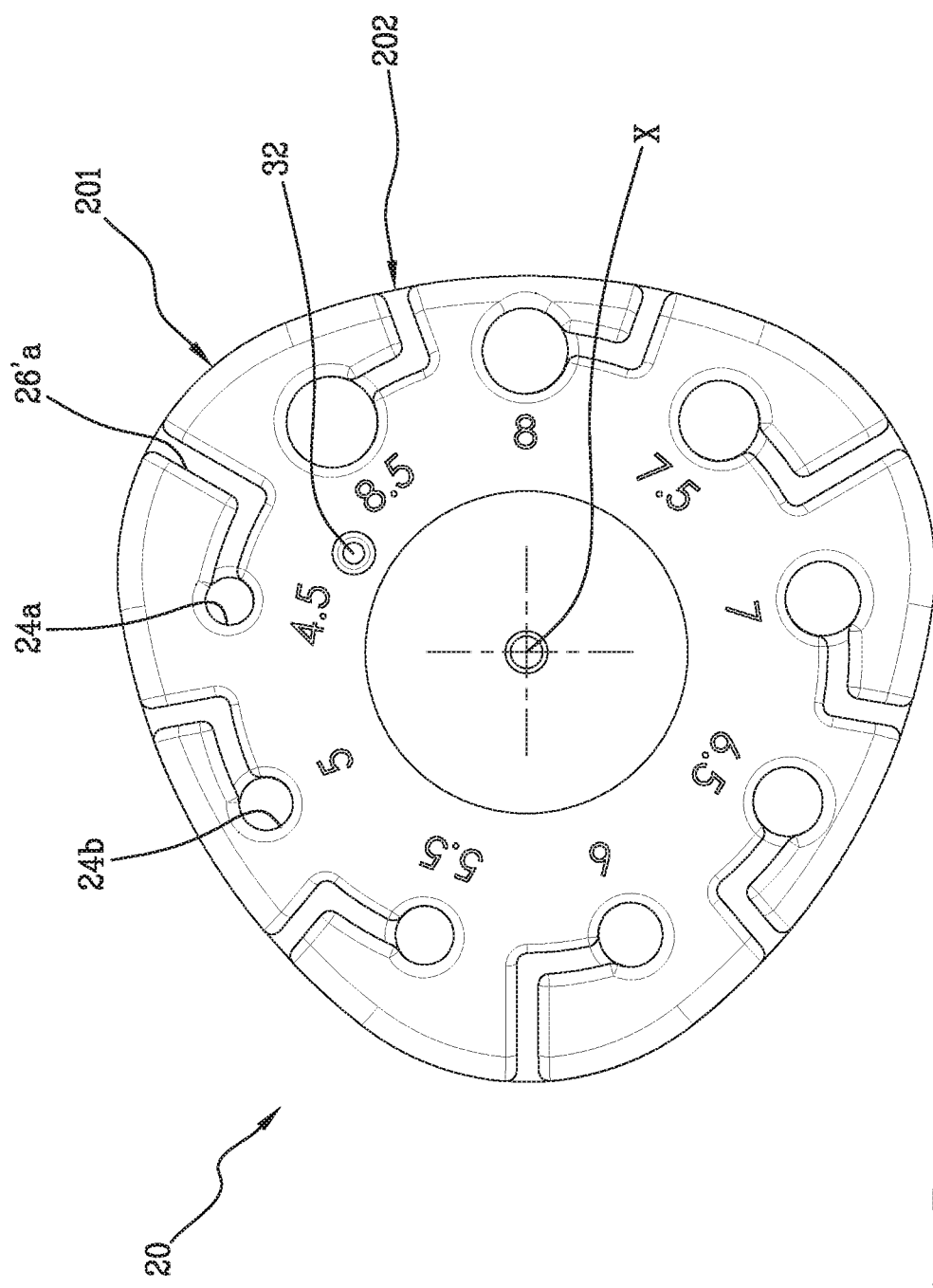
FIG. 5 shows an axial view of the graft measuring template in FIG. 4, in a closed configuration.
Figure 6:
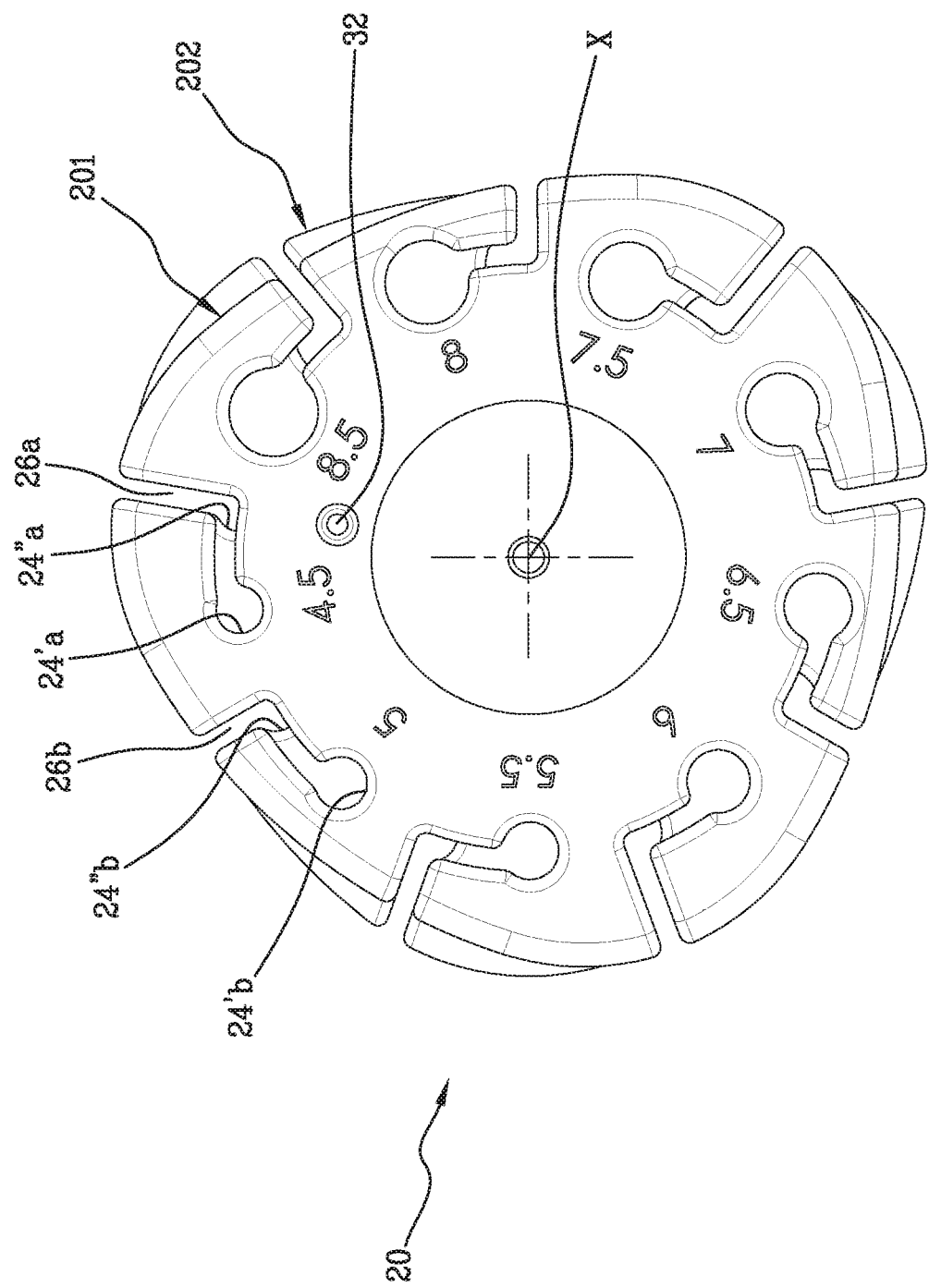
FIG. 6 shows an axial view of the graft measuring template in FIG. 4, in an open configuration.
Figure 7:
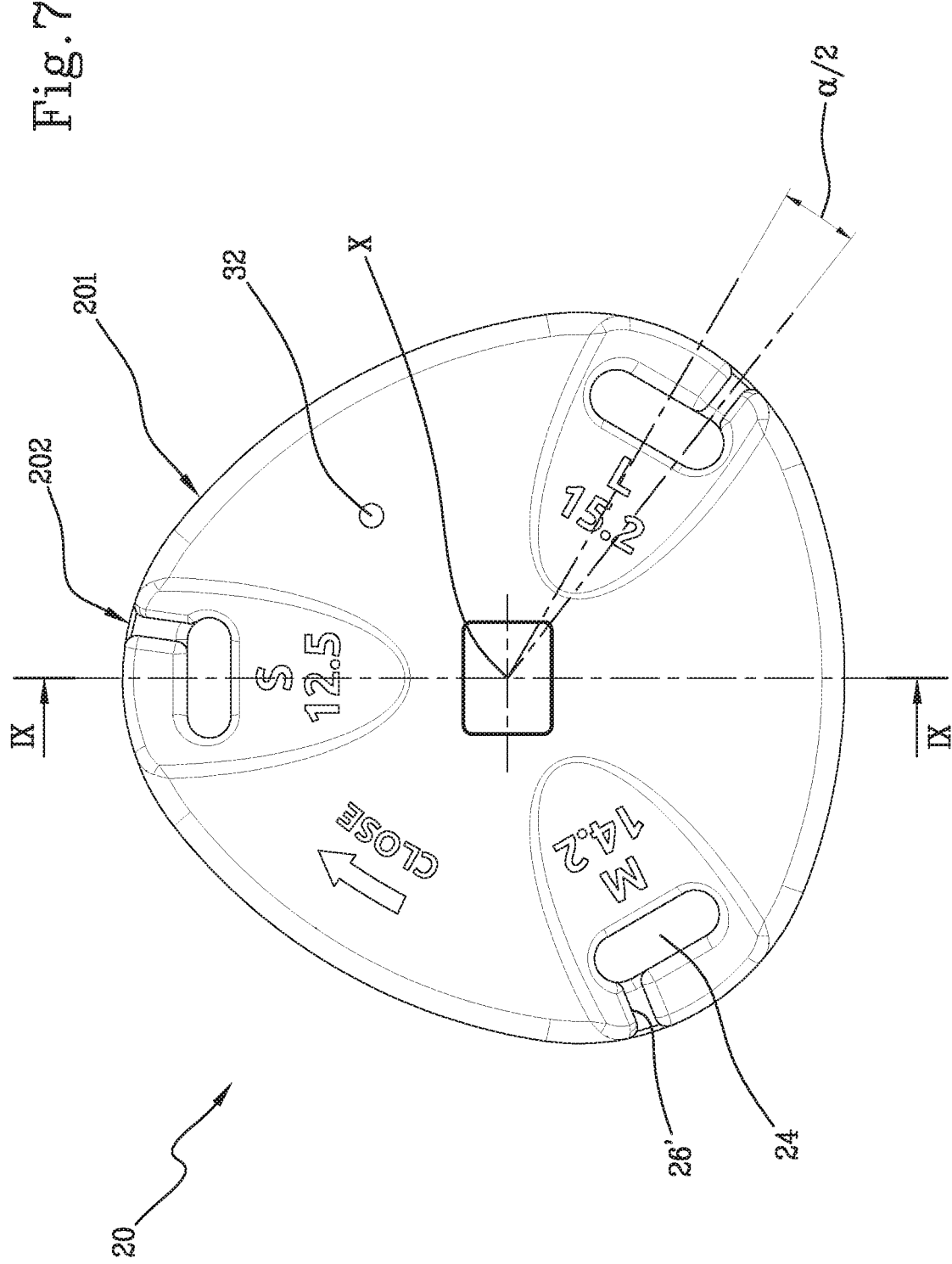
FIG. 7 shows a first axial view of a graft measuring template according to the invention.
Figure 8:
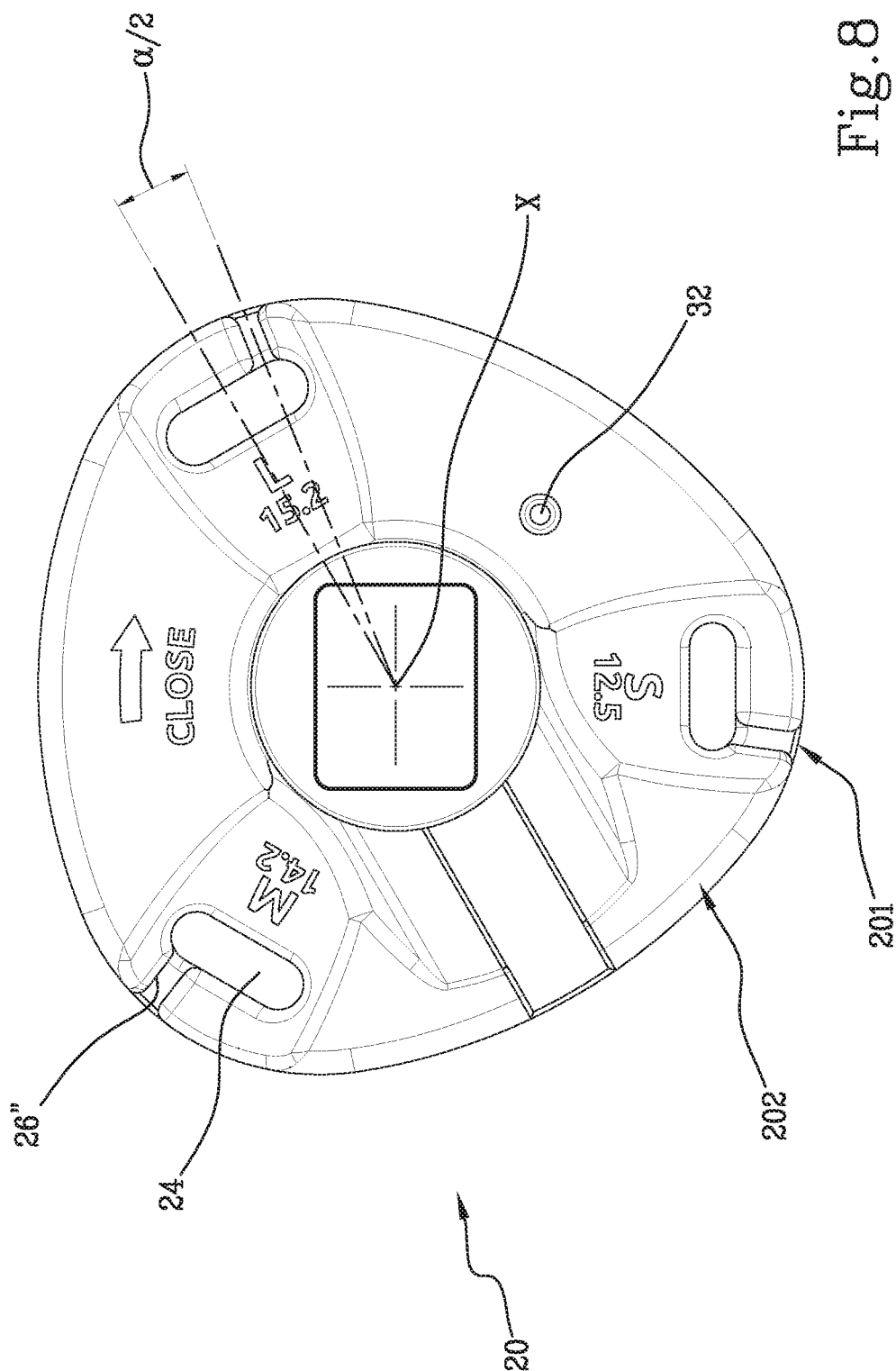
FIG. 8 shows a second axial view of the graft measuring template in FIG. 7.
Figure 9:
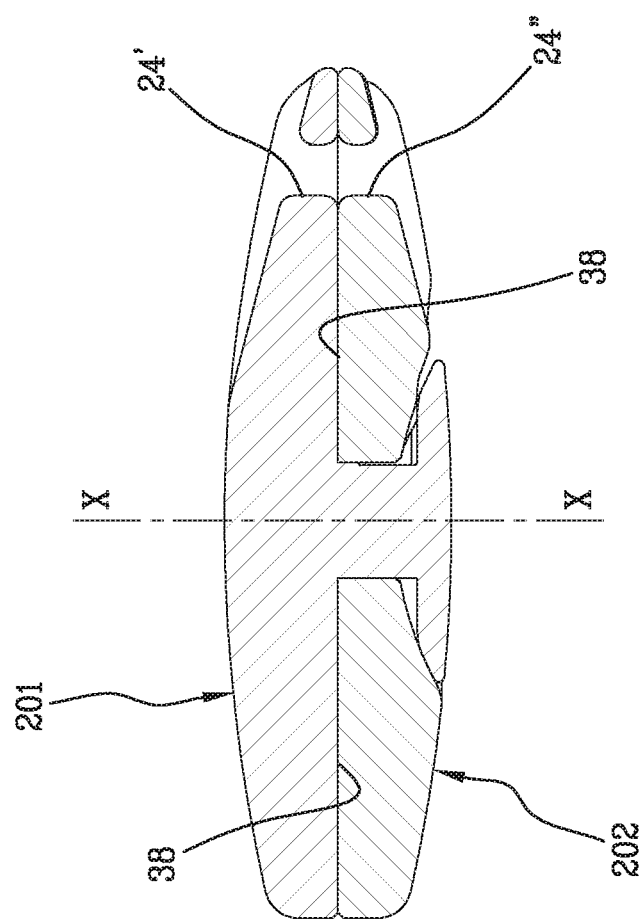
FIG. 9 shows the cross section taken along the line IX-IX in FIG. 7.
Figure 10:
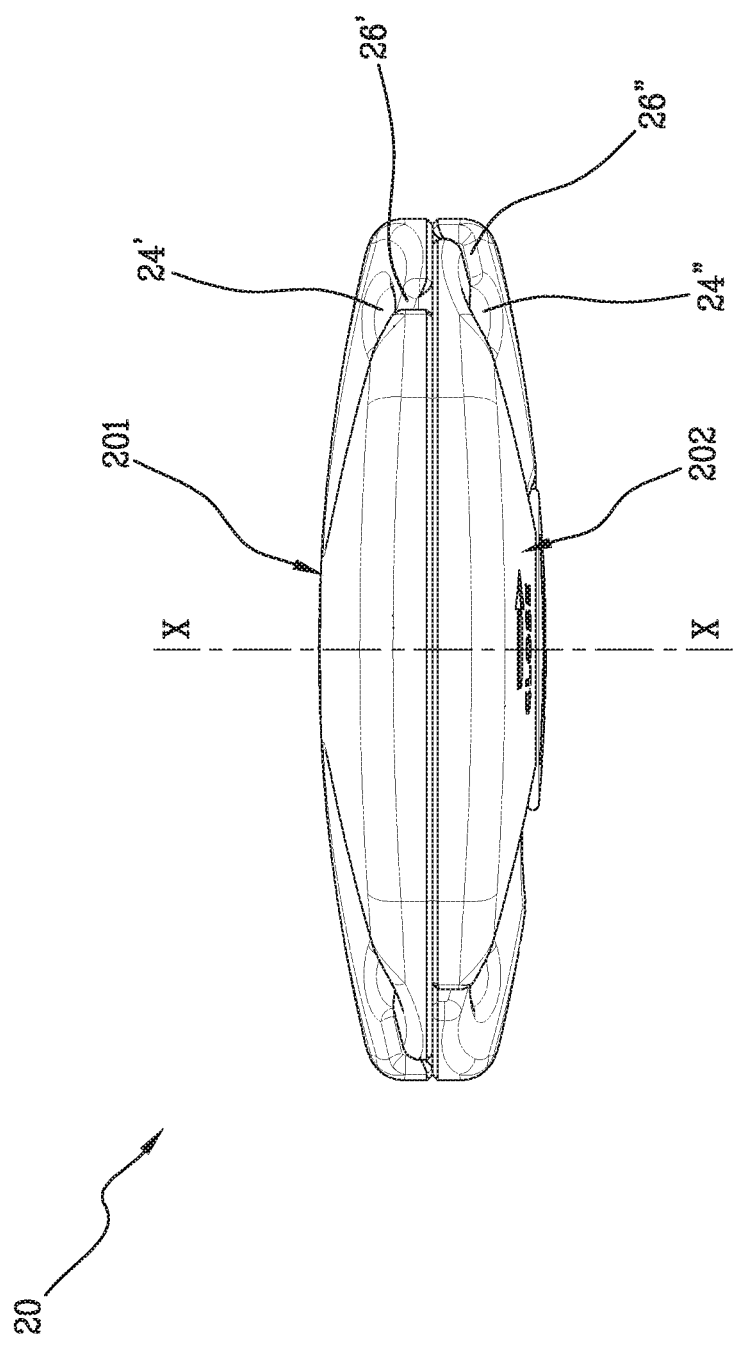
FIG. 10 shows a radial view of the graft measuring template in FIG. 7.

Preferably, each of the two half-bodies 201, 202 comprises an equal series of openings $24_a$, $24_b$, $24_c$ . . . . That is, for each opening $24'_a$ of the first half-body 201 it is possible to identify an opening $24''_a$ of the second half-body 202 conjugated to it. Such feature is evident in FIG. 3, where the two disassembled half-bodies 201, 202 of the template 20 in FIG. 2 are shown. In FIG. 3, the two half-bodies 201, 202 were opened like a book, starting from the template 20 in the closed position C (as shown in FIG. 2), and rotating them by 180° relative to each other about axis R. Both half-bodies 201, 202 each show the relative inner surface 38, i.e. that surface which, in use, faces the interior of the template 20. During the use of the template 20, the two inner surfaces 38 shown in FIG. 3 are then placed side by side. Similar considerations can be made by comparing FIGS. 7 and 8 showing the two axially opposite faces of the same template 20.

Preferably, two openings $24'_a$, $24''_a$ conjugated to each other and placed each on one of the two half-bodies 201, 202 have equal shape, equal size and equal radial distance from the axis X. These equalities cause, in the closed position C of the template 20, the two conjugated openings $24'_a$, $24''_a$ to overlap perfectly.

As already mentioned above, the slots 26 extend at least partially in a radial direction. As can be seen again in FIG. 3 or by comparing FIGS. 7 and 8 to each other, considering two conjugated openings $24'_a$, $24''_a$, at least one of the two relative slots $26'_a$ or $26''_a$ is not aligned in the radial direction with the centre of the respective opening $24'_a$ or $24''_a$. In the example of FIG. 3, each of the slots $26''_a$ of the second half-body 202 (left) is radially aligned with the centre of the respective opening $24''_a$. By contrast, all the slots $26'_a$ of the first half-body 201 (right) are radially misaligned with respect to the centre of the respective openings $24'_a$ and are moved in a circumferential direction by a given angle. By contrast, in the example of FIGS. 7 and 8, all the slots $26'_a$, $26''_a$ of both half-bodies 201, 202 are radially misaligned with respect to the centre of the respective openings $24'_a$, $24''_a$ and are moved in a circumferential direction by a given angle.

Preferably, considering a pair of conjugated openings $24'_a$, $24''_a$, the sum of the circumferential displacement angles of the two relative slots $26'_a$, $26''_a$ equals in absolute value the angle $\alpha$ separating the open position A from the closed position C of the template 20. In the example of FIG. 3, since the circumferential displacement of the slots $26''_a$ of the second half-body 202 (left) is zero, the circumferential displacement angle of the slots $26'_a$ of the first half-body 201 (right) equals exactly the angle $\alpha$. In the example of FIGS. 7 and 8, since the circumferential displacement of the slots $26'_a$, $26''_a$ of the two half-bodies 201, 202 is the same, each of the angles equals ½ $\alpha$.

Figure 11:
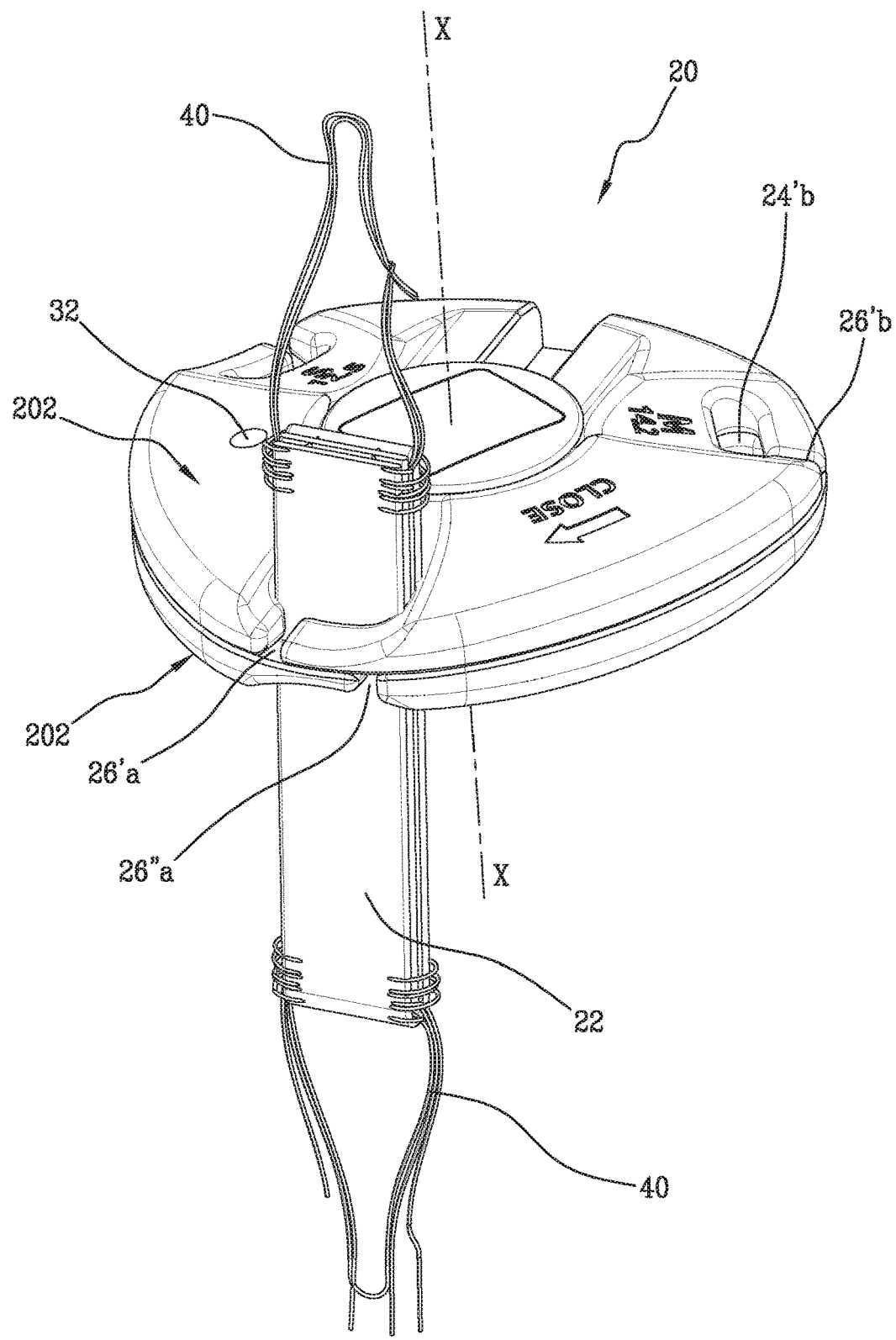
FIG. 11 shows a perspective view of the graft measuring template in FIG. 7, in a closed configuration in use.

In the embodiments illustrated in the accompanying FIGS. 2 to 6, the templates 20 according to the invention comprise circular openings 24. Otherwise, in the embodiment illustrated in the accompanying FIGS. 7-8 and 11, the template 20 according to the invention comprises elongated openings 24, in particular having an oval shape with two sides substantially straight and parallel to each other. These and other different shapes of the openings 24 are advantageous to approximate the shape of the transverse cross section of the graft 22, which may take different shapes as appropriate. The use of openings 24 that approximate the shape of the cross section of the graft 22 has the advantage of allowing its measurement without introducing an excessive deformation.

In the embodiments illustrated in the accompanying figures, the two half-bodies 201, 202 and, accordingly, the template 20 as a whole, take a discoidal shape. Such shape, although not strictly necessary, is very suitable to the mutual rotation of the two half-bodies 201, 202 around the axis X. In addition, the discoidal shape allows the overall size of the template 20 to be limited, while maximizing its peripheral extension in order to arrange more easily the plurality of openings 24.

According to another aspect, the invention relates to a method for measuring the cross section of a graft 22, wherein the method comprises the steps of:
providing a template 20 according to the above description;
providing a graft 22 comprising, on at least one end, suture threads 40;
providing the template 20 in the open position A;
estimating a size of the cross section of the graft 22;
identifying in the template 20 the first-attempt opening $24_1$ corresponding to the estimated size of the cross section of the graft 22;
radially introducing the suture threads 40 in the slot 261 of the first-attempt opening $24_1$;
sliding the suture threads 40 into the first-attempt opening $24_1$;
rotating the one with respect to the other the two half-bodies 201, 202 of the template 20 so as to bring them in the closed position C;
sliding the template 20 along the suture threads 40 so as to approach the first-attempt opening $24_1$ to the end of the graft 22; and
trying to axially introduce the graft 22 in the first-attempt opening $24_1$.

According to the method of the invention, it is necessary to evaluate which of the three possible conditions is verified: the graft 22 slides in the first-attempt opening $24_1$ without interference and without clearance; or the graft 22 easily enters the first-attempt opening $24_1$ and slides therein with clearance; or the graft 22 does not enter the first-attempt opening $24_1$ at all, or it does not enter easily and hardly slides therein.

Preferably, if the graft 22 slides into the first-attempt opening $24_1$ without interference and without clearance, the first-attempt opening $24_1$ provides the correct size of the graft 22, based on which the bone tunnel is to be made.

Preferably, if the graft 22 easily enters the first-attempt opening $24_1$ and slides therein with clearance, then the method involves:
pulling the suture threads 40 out of the first-attempt opening $24_1$;
identifying in the template 20 a second-attempt opening $24_2$, smaller than the first-attempt opening $24_1$; and
repeating the steps of the method from the step of providing the template 20 in the open position A on.

Preferably, if the graft 22 lastly does not enter at all the first-attempt opening $24_1$, or does not enter it easily and slide therein with difficulty, then the method involves:
pulling the suture threads 40 out of the first-attempt opening $24_1$;
identifying in the template 20 a second-attempt opening $24_2$, larger than the first-attempt opening $24_1$; and
repeating the steps of the method from the step of providing the template 20 in the open position A on.

The method of the invention may be repeated several times, with n attempts, until the condition in which the graft 22 slides into the identified opening 24 without interference and without clearance occurs. The size of this opening 24 represents the correct size of the cross section of the graft 22, based on which the bone tunnel is to be made.

As the skilled person can well understand, in the various repetitions of the method, the description of the steps set forth above still applies, provided that "first attempt" is replaced with "nth attempt", and "second attempt" with "(n+1)th attempt".

In some embodiments, the method may also involve the step of providing two different templates 20, wherein a first template 20 comprises a first set of openings $24_a$, $24_b$, $24_c$ . . . relating to a first range of sizes, and wherein a second template 20 comprises a second set of openings $24_p$, $24_q$, $24_r$ . . . relating to a second range of sizes.

As the skilled person can easily understand, the invention allows to overcome the drawbacks highlighted previously with reference to the prior art.

In particular, the present invention provides a measuring template 20 and method that respectively allow the size of the cross section of a graft 22 to be determined without any risk of error.

Furthermore, the present invention provides a measuring template 20 and method that continue to provide the advantages of solutions of known type, in addition to the advantages introduced.

It is clear that the specific features are described in relation to various embodiments of the invention, by way of non-limiting example. Obviously, one skilled in the art may make further modifications and variations to this invention, in order to meet contingent and specific requirements. For example, the technical features described in connection with an embodiment of the invention may be extrapolated from it and applied to other embodiments of the invention. Besides, such modifications and variations are comprised within the scope of the invention, as defined by the following claims.

The invention claimed is:

1. A template for measuring the cross section of a graft, the template comprising a first half-body and a second half-body, wherein:
the two half-bodies are mutually secured such that they can rotate the one with respect to the other around an axis;
each one of the two half-bodies comprises a plurality of openings having known and different sizes;
each one of the openings of the two half-bodies is open toward the outside through an at least partially radial slot;
and wherein the two half-bodies can rotate the one with respect to the other around the axis between an open position and a closed position and vice versa, wherein:
in the open position, the slots of the first half-body axially coincide with the slots of the second half-body; and
in the closed position the openings of the first half-body axially coincide with the openings of the second half-body.

2. The template according to claim 1, wherein the openings are preferably arranged in proximity of the radial periphery of the two half-bodies.

3. The template according to claim 1, wherein the mutual rotation of the two half-bodies is limited within a predefined angle.

4. The template according to claim 1, further comprising a stop of the type having a spring-loaded ball, suitable for marking the reaching of the closed position.

5. The template according to claim 1, wherein each one of the two half-bodies comprises an equal series of openings.

6. The template according to claim 1, wherein for each opening of the first half-body it is possible to identify a conjugated opening of the second half-body.

7. The template according to claim 6, wherein two conjugated openings have equal shape, equal size and equal radial distance from the axis.

8. The template according to claim 6, wherein in two conjugated openings, at least one of the two relative slots is not aligned in the radial direction with the centre of the respective opening.

9. A method for measuring the cross section of a graft, comprising the steps of:
providing a template according to claim 1;
providing a graft comprising suture threads at at least one end;
estimating a size of the cross section of the graft;
identifying in the template a first-attempt opening corresponding to the estimated size of the cross section of the graft;
providing the template in the open position;
radially introducing the suture threads in the slot of the identified first-attempt opening;
sliding the suture threads into the identified first-attempt opening;
rotating the one with respect to the other the two half-bodies of the template so as to bring them in the closed position;
sliding the template along the suture threads so as to approach the identified first-attempt opening to the end of the graft;
trying to axially introduce the graft in the identified first-attempt opening; and
evaluating which condition is verified from the following possible conditions: the graft slides in the identified first-attempt opening without interference and without clearance; or the graft enters the identified first-attempt opening and slides therein with clearance; or the graft does not enter the identified first-attempt opening at all, or the graft enters the first-attempt opening but slides with interference.

10. The method according to claim 9, wherein, if the graft slides in the identified opening without interference and without clearance, then the method further comprises the step of obtaining the correct size of the graft from the size of the identified opening.

11. The method according to claim 9, wherein, if the graft enters the identified opening and slides therein with clearance, then the method further comprises the steps of:
pulling the suture threads out of the previously identified opening;
identifying in the template a subsequent attempt opening, smaller than the opening identified in the previous attempt; and
repeating the steps of the method from the step of providing the template in the open position on.

12. The method according to claim 9, wherein, if the graft does not enter the identified opening at all, or it does not enter easily and hardly slides therein, then the method further comprises the steps of
pulling the suture threads out of the previously identified opening;
identifying in the template a subsequent attempt opening, larger than the opening identified in the previous attempt; and
repeating the steps of the method from the step of providing the template in the open position on.

13. The method according to claim 9, further comprising the step of providing two different templates, wherein a first template comprises a first series of openings relating to a first range of sizes, and wherein a second template comprises a second series of openings relating to a second range of sizes.

* * * * *